United States Patent
Simic

(10) Patent No.: US 10,088,432 B2
(45) Date of Patent: Oct. 2, 2018

(54) SYNTHETIC DIAMOND LABELLING AND IDENTIFICATION SYSTEM AND METHOD

(71) Applicant: Dusan Simic, New York, NY (US)

(72) Inventor: Dusan Simic, New York, NY (US)

(73) Assignee: Dusan Simic, New York, NY (US)

( * ) Notice: Subject to any disclaimer, the term of this patent is extended or adjusted under 35 U.S.C. 154(b) by 0 days.

(21) Appl. No.: 15/686,247

(22) Filed: Aug. 25, 2017

(65) Prior Publication Data

US 2018/0067056 A1 Mar. 8, 2018

Related U.S. Application Data

(60) Provisional application No. 62/383,057, filed on Sep. 2, 2016.

(51) Int. Cl.

| | | |
|---|---|---|
| *G01N 21/88* | (2006.01) | |
| *G01N 21/87* | (2006.01) | |
| *C30B 29/04* | (2006.01) | |
| *C30B 33/02* | (2006.01) | |
| *C30B 33/04* | (2006.01) | |
| *G01N 21/64* | (2006.01) | |
| *G09F 3/02* | (2006.01) | |
| *C23C 14/06* | (2006.01) | |
| *C23C 14/48* | (2006.01) | |

(52) U.S. Cl.
CPC ...... *G01N 21/8803* (2013.01); *C23C 14/0611* (2013.01); *C23C 14/48* (2013.01); *C30B 29/04* (2013.01); *C30B 33/02* (2013.01); *C30B 33/04* (2013.01); *G01N 21/6447* (2013.01); *G01N 21/87* (2013.01); *G09F 3/02* (2013.01)

(58) Field of Classification Search
CPC ..... C23C 14/0611; C23C 14/48; C30B 29/04; C30B 33/02; C30B 33/04; G01N 21/6447; G01N 21/87; G01N 21/8803; G09F 3/02
See application file for complete search history.

(56) References Cited

U.S. PATENT DOCUMENTS

| | | | | |
|---|---|---|---|---|
| 5,883,389 | A * | 3/1999 | Spear | G01N 21/87 |
| | | | | 250/461.1 |
| 2015/0112643 | A1* | 4/2015 | Khan | G01N 21/35 |
| | | | | 702/189 |
| 2016/0052789 | A1* | 2/2016 | Gaathon | C01B 31/065 |
| | | | | 216/24 |
| 2016/0161420 | A1* | 6/2016 | Zhu | G01N 27/041 |
| | | | | 374/44 |
| 2017/0010217 | A1* | 1/2017 | Paleari | G01N 21/87 |

* cited by examiner

*Primary Examiner* — Mark R Gaworecki
(74) *Attorney, Agent, or Firm* — Scarinci Hollenbeck, LLC

(57) ABSTRACT

A synthetic diamond labelling and identification method comprising the steps of selecting a synthetic diamond with between 200 and 600 parts per billion of an isolated substitution Nitrogen atoms within its lattice structure, irradiating the selected synthetic diamond with a beam energy that is equal to at least one-half the height of the selected diamond, maintaining the temperature of the selected diamond below 500 degrees Celsius while it is being irradiated, annealing the irradiated selected diamond as to create a plurality of nitrogen-vacancy centers without changing the original color of the selected diamond, and generating a bulk luminesces visible to the naked eye by exciting the plurality of created nitrogen-vacancies with an ultraviolet lamp.

12 Claims, 8 Drawing Sheets

|  | IRRADIATION | | | ANNEALING | |
|---|---|---|---|---|---|
| AMOUNT OF NITROGEN | SIZE | MeV | TIME | HIGH VACUUM AT 900°C | LPHT IN HYDROGEN AT 1800°C |
| 200-600 ppb OF SINGLE NITROGEN | 0.005-0.07 CT | 1 | 10 MIN | 10 MIN | 2-3 MIN |
| | 0.07-0.30 CT | 1.2 | 10-12 MIN | 10-12 MIN | 3-4 MIN |
| | 0.30-1 CT | 1.5 | 12-14 MIN | 12-13 MIN | 4-5 MIN |
| | 1+ CT | 2.0 | 15-18 MIN | 14-15 MIN | 5-6 MIN |
| 600-1000 ppb OF SINGLE NITROGEN | 0.005-0.07 CT | 1 | 8-10 MIN | 9-10 MIN | 2 MIN |
| | 0.07-0.30 CT | 1.2 | 10 MIN | 10-11 MIN | 2 MIN |
| | 0.30-1 CT | 1.5 | 12 MIN | 11-12 MIN | 3 MIN |
| | 1+ CT | 2.0 | 15 MIN | 12-13 MIN | 4 MIN |
| 1 ppm OF SINGLE NITROGEN | 0.005-0.07 CT | 1 | 8 MIN | 8-9 MIN | 1-2 MIN |
| | 0.07-0.30 CT | 1.2 | 10 MIN | 9-10 MIN | 1-2 MIN |
| | 0.30-1 CT | 1.5 | 12 MIN | 10-11 MIN | 2 MIN |
| | 1+ CT | 2.0 | 13 MIN | 11-12 MIN | 3 MIN |

FIG. 9

SYNTHETIC DIAMOND LABELLING AND IDENTIFICATION SYSTEM AND METHOD

FIELD OF THE INVENTION

This disclosure relates generally to a syndetic diamond labelling and identification system and method.

BACKGROUND

The labelling and identification of synthetic diamonds is a complex and costly process, especially if the diamonds are mounted. All existing automated identification systems identify only round and loose diamonds. After identification, the labs which implement these systems provide a warranty only if the diamonds are in a sealed bag. Once the sealed special bag has been opened, all loose and mounted diamonds are no longer under warranty. As a result, subsequent manipulation of the diamonds cannot be prevented. Also, unintentional mistakes (change of diamonds in setting process) during jewelry production also cannot be prevented and cannot be easily recognized in the final product.

However, synthetic diamond production is a dynamic process. It is possible to change production parameters and to implement some post production treatments to purposely create defects in the synthetic diamond lattice that existing identification systems and applied algorithms will not recognize.

SUMMARY

The present disclosure explains the creation of optically invisible defects in the visible range of the electromagnetic spectrum resulting in a bulk luminescence within a synthetic diamond that is easily visible to the naked eye under specific excitations. The method of the present disclosure will provide for the clear and easy separation, identification, and screening (for gemological laboratories, diamond dealers, jewelry producers and retailers and for customers) of synthetic diamonds without altering their original color. The methods of the present disclosure also provide for the branding of one specific production of synthetic diamonds making this production unique and recognizable.

An exemplary embodiment, a synthetic diamond labelling and identification method is disclosed comprising the steps of selecting a synthetic diamond with between 200 and 600 parts per billion of an isolated substitution (single) Nitrogen atoms within its lattice structure, irradiating the selected synthetic diamond with a beam energy that is equal to at least one-half the height of the selected diamond, maintaining the temperature of the selected diamond below 500 degrees Celsius while it is being irradiated, annealing the irradiated selected diamond as to create a plurality of nitrogen-vacancy centers without changing the original color of the selected diamond, and generating a bulk luminesces visible to the naked eye by exciting the plurality of created nitrogen-vacancies with an ultraviolet lamp.

In another exemplary embodiment, a synthetic diamond labelling and identification method is disclosed comprising the steps of selecting a synthetic diamond with between 600 and 1000 parts per billion of isolated substitution (single) Nitrogen atoms within its lattice structure, irradiating the selected synthetic diamond with a beam energy that is equal to at least one-half the height of the selected diamond, maintaining the temperature of the selected diamond below 500 degrees Celsius while it is being irradiated, annealing the irradiated selected diamond as to create a plurality of nitrogen-vacancy centers without changing the original color of the selected diamond, and generating a bulk luminesces visible to the naked eye by exciting the plurality of created nitrogen-vacancies with an ultraviolet lamp.

In yet another exemplary embodiment, a synthetic diamond labelling and identification method is disclosed comprising the steps of selecting a synthetic diamond with more than 1000 parts per billion of isolated substitution (single) Nitrogen atoms within its lattice structure, irradiating the selected synthetic diamond with a beam energy that is equal to at least one-half the height of the selected diamond, maintaining the temperature of the selected diamond below 500 degrees Celsius while it is being irradiated, annealing the irradiated selected diamond as to create a plurality of nitrogen-vacancy centers without changing the original color of the selected diamond, and generating a bulk luminesces visible to the naked eye by exciting the plurality of created nitrogen-vacancies with an ultraviolet lamp.

DEFINITIONS

Bulk luminescence refers to the emission of a pink or red fluorescence from the whole of a synthetic diamond in response to a defined excitation, and not an emission from specific growth sectors or points within the synthetic diamond.

BRIEF DESCRIPTION OF THE DRAWINGS

FIG. 9 is a table showing parameters used in the synthetic diamond labelling and identification method according to the disclosed embodiment.

DETAILED DESCRIPTION OF THE INVENTION

Figure 1:
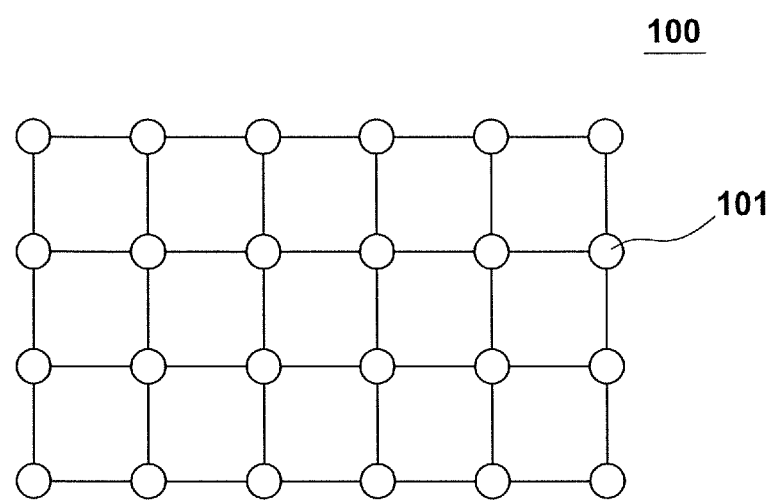
FIG. 1 is a two-dimensional representation of the lattice of a perfect diamond.

In FIG. 1, a two-dimensional representation of the lattice of a perfect diamond is shown. As shown in FIG. 1, this lattice structure 100 is comprised of carbon atoms 101 that are each symmetrically surrounded by four other carbon atoms 101. This lattice structure does not contains any impurities, including any Nitrogen or Boron atoms.

Figure 2:
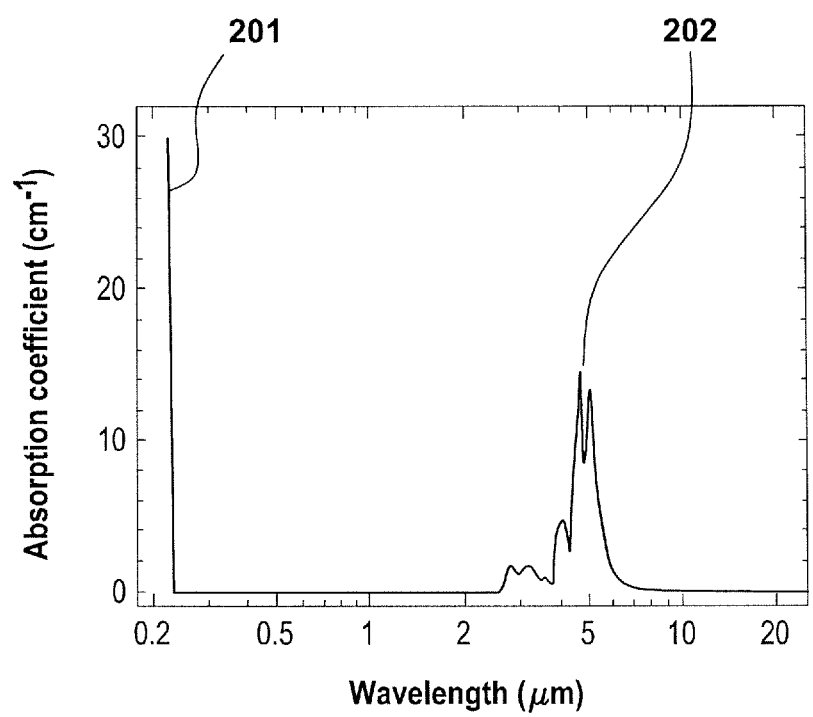
FIG. 2 is a spectroscopic absorption graph for a perfect diamond.

In FIG. 2, a spectroscopic absorption graph of the perfect diamond is shown. As shown in FIG. 2, a perfect diamond, without any impurities such as Nitrogen or Boron atoms, will absorb light solely at the so-called absorption edge wavelength of approximately 230 nanometers 201. A perfect diamond will also absorb light within the infrared wavelength region between 2500-7500 nanometers, the so-called 2 and three 3 photon region 202. If these perfect diamond are excited using any kind of light, neither visible nor invisible photo-luminescence will be induced. In other words, it is not possible to create a pink or red fluorescence in a perfect diamond without any impurities, namely impurities including Nitrogen and Boron atoms.

Figure 3:
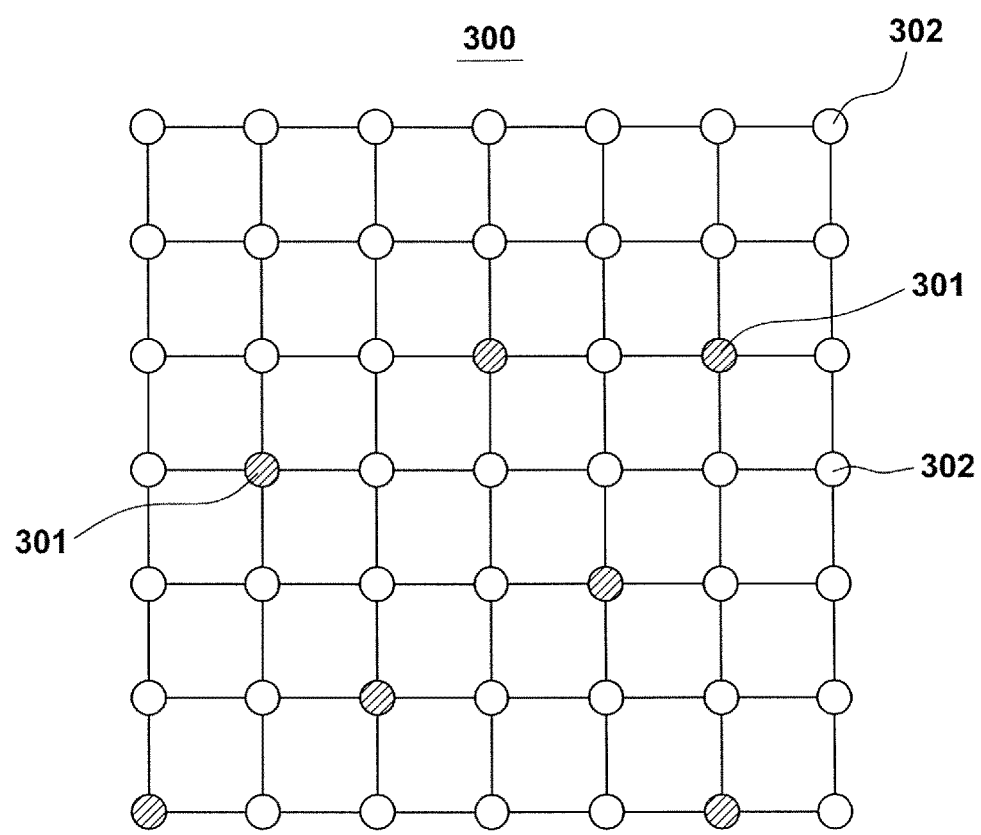
FIG. 3 is a two dimensional representation of the lattice of a synthetic diamond lattice selected for the synthetic diamond labelling and identification system and method according to the disclosed embodiment.

In FIG. 3, a two dimensional representation of the lattice of a synthetic diamond lattice selected for the synthetic diamond labelling and identification system and method according to the disclosed embodiment is shown. As shown in FIG. 3, this lattice structure 300 includes carbon atoms 302 as well as impurities in the form of isolated substitution (single) Nitrogen atoms 301. These isolated substitution (single) Nitrogen atom impurities are necessary for the creation of nitrogen-vacancies (N-V) centers which will eventually result in emission of a visible bulk luminescence under specific excitation.

Figure 4:
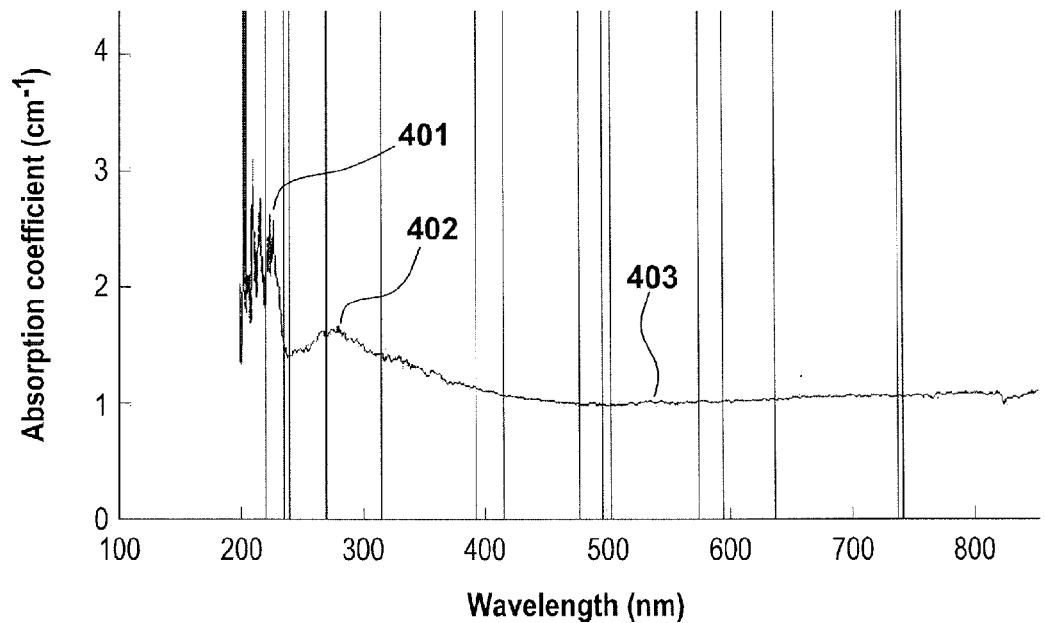
FIG. 4 is a spectroscopic absorption graph of the selected synthetic diamond before being processed by the synthetic diamond labelling and identification method according to the disclosed embodiment.

In FIG. 4, a spectroscopic absorption graph of the selected synthetic diamond before being processed by the synthetic diamond labelling and identification method according to the disclosed embodiment is shown. As shown in FIG. 4, as with the perfect diamond lattice, light is absorbed at the so-called absorption edge wavelength at approximately 230 nanometers 401. Unlike the perfect diamond lattice, light is now also absorbed at 270 nanometers 402 which reflects the presence of Nitrogen atom impurities. Importantly, there is also some absorption in the visible range of electromagnetic spectrum between 400 and 700 nanometers 403 characteristic of a so called colorless or near-colorless diamond under the 4C color grading standard.

Figure 5:
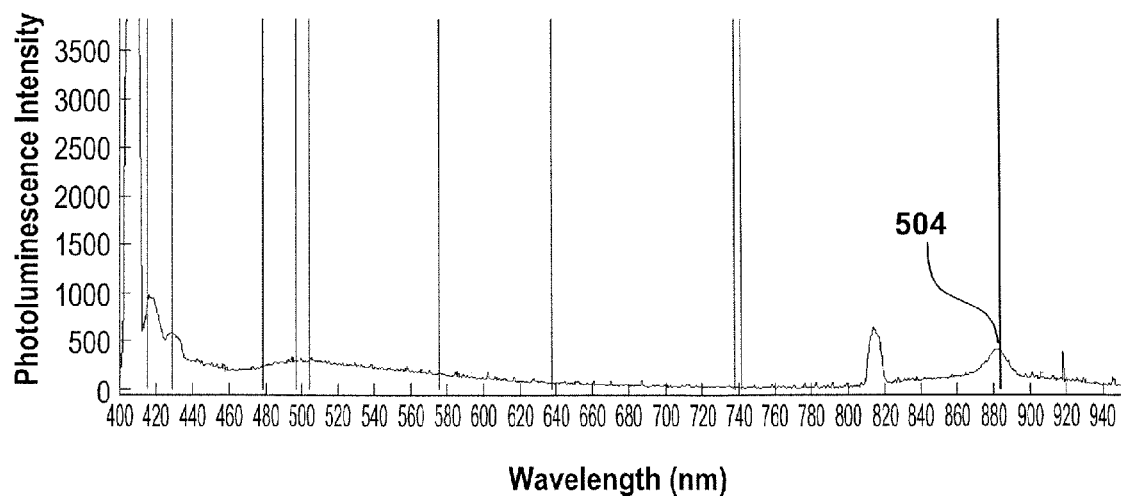
FIG. 5 is a spectroscopic photoluminescence of the selected synthetic diamond before being processed by the synthetic diamond labelling and identification method according to the disclosed embodiment.

In FIG. 5, a spectroscopic photoluminescence of the selected synthetic diamond before being processed by the synthetic diamond labelling and identification method according to the disclosed embodiment is shown. As shown in FIG. 5, there is some photoluminescence emission at 405 nanometers 501 caused by the presence of Nickel (Ni) as a necessary part of the solvent catalyst alloy. The metal solvent catalysts are used to decrease the activation barrier of graphite to diamond transformation. This is necessary in order to decrease the pressure and temperature parameter required for diamond formation to values achievable in current production systems. The most commonly used and effective solvent-catalyst are alloys of the iron of metal, including iron (Fe), nickel (Ni), and Cobalt (Co).

Figure 6:
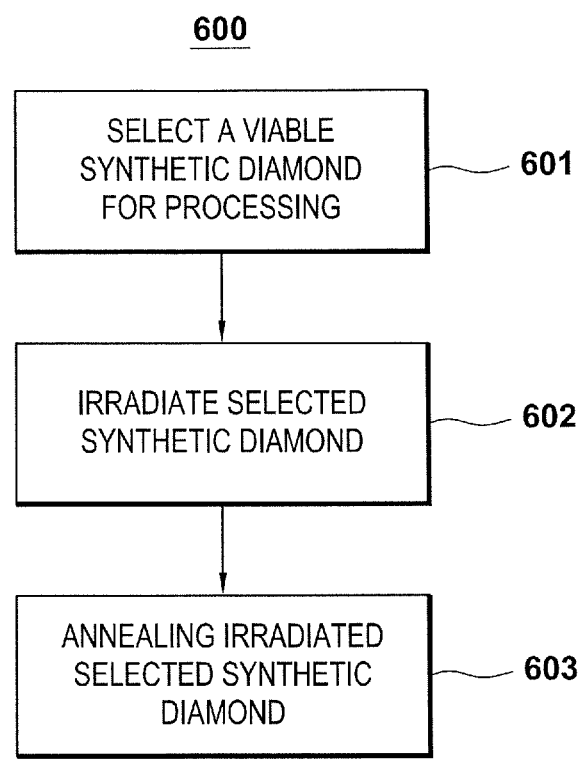
FIG. 6 is a flow chart of the synthetic diamond labelling and identification method according to the disclosed embodiment.

In FIG. 6, a flow chart of the synthetic diamond labelling and identification method according to the disclosed embodiment is shown. As shown in FIG. 6, the method 600 begin with the selection of a viable synthetic diamond in step 601. A viable synthetic diamond is any synthetic diamond having at least 200 parts per billion of an isolated substitute (single) Nitrogen atom impurities. These include both high-pressure high-temperature ("HPHT") synthetic diamonds and chemical vapor deposition ("CVD") synthetic diamonds. The method of the present disclosure may be performed on rough, blocked or polished HPHT grown synthetic diamonds as well as on lasered, blocked, or polished CVS grown synthetic diamonds.

Once a viable synthetic diamond has been selected, the selected synthetic diamond is irradiated with energized particles in step 602. This irradiation creates the vacancies within the diamond lattice necessary for the subsequent formation of the N-V centers within the selected diamond. The irradiation may be done using electrons, neutrons, alpha particles, gamma rays or any other irradiation means know to a person of ordinary skill in the art. Specifically, energized particles are fired at the synthetic diamond to displace some of the Carbon atoms within its lattice structure thereby creating vacancies with the displaced Carbon atoms now placed into interstitial positions within that lattice. In the case of an electron irradiation bean, the minimum beam energy is equal to at least half of the height of the selected diamond. For example, for 1 carat diamond, where height of the diamond is approx. 4 mm, the minimum the electron beam energy is 2 MeV as to allow the particle bean to penetrate approximately 2 mm into the selected 1 carat diamond.

In order to prevent the creation of unwanted defects with the selected diamond due to an increased in temperature during irradiation, it is necessary to maintain the temperature of the selected diamond below 500 degrees Celsius.

Working under the assumption that it takes 10 electron within an irradiation beam to create a single vacancy, it is necessary to irradiate the selected diamond with a fluence of $<2 \times 10^{16}$ $cm^{-2}$, this fluence number referring a stream of particles crossing a unit area within eth selected diamond. The duration of irradiation is dependent on the number isolated Nitrogen atoms with the selected diamond.

In order to achieve bulk luminance, the vacancies must the created throughput the interior of the selected synthetic diamond and not only on the surface or in portions of the diamond. As such, the width of the irradiation particle beam must encompass the whole of the synthetic diamond and not just a portion or area. This ensures that the created vacancies are not localized within a specific portion or area of the synthetic diamond. Moreover, the amount of energy deposited in a diamond due to irradiation must be of a sufficient strength as to penetrate to at least the center portion within the synthetic diamond.

As an example, a one carat synthetic diamond will have an approximate width of 6.5 millimeters and an approximate depth (height) of 4.0 millimeters. An electron irradiation beam having 1 MeV of acceleration energy is capable of penetrating a distance of approximately 1 millimeter into a synthetic diamond. As such, an electron irradiation beam having a minimum beam width of at least 6.5 millimeters and a minimum of 2 MeV of acceleration energy is necessary for a one carat synthetic diamond.

Taking the acceleration energy of the particle beam as a fixed value based on the size of the synthetic diamond, the quantity of vacancies created within the synthetic diamond is a function of the fluence of the produced electrons and the duration that the synthetic diamond is exposed to the irradiation beam. A sufficient number of vacancies are required for the creation of the minimum amount of N-V centers necessary to produce a visible bulk luminescence from within the synthetic diamond. The required number of vacancies relative to the number of single Nitrogen atoms required to achieve bulk luminescence is shown below in Table 1.

TABLE 1

| Single Nitrogen (ppb) | Vacancies (ppb) |
|---|---|
| 200-600 | 200-1200 |
| 600-1000 | 200-1000 |
| 1000+ | 200-800 |

The creation of too many vacancies may detrimentally affect the original color of the synthetic diamond.

Figure 7:
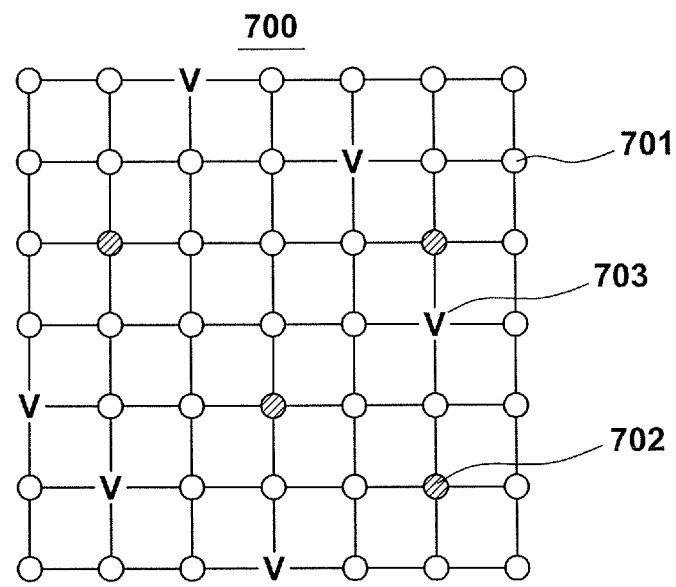
FIG. 7 is a two dimensional representation of the selected synthetic diamond lattice irradiated in the synthetic diamond labelling and identification method according to the disclosed embodiment.

In FIG. 7, a two dimensional representation of the selected synthetic diamond lattice irradiated in the synthetic diamond labelling and identification method according to the disclosed embodiment is shown. As shown in FIG. 7, the irradiated lattice 700 now includes the original carbon atoms 701 as well as Nitrogen atom 702 impurities and newly formed vacancies 703 resulting from the irradiation of the synthetic diamond.

Returning to FIG. 6, once the synthetic diamond has been irradiated, the irradiated synthetic diamond is annealed at a high temperature in step 603. When synthetic diamonds with vacancies are heated at high temperatures, the vacancies become mobile and are eventually captured by the Nitrogen atoms within the diamond's lattice and thereby creating a N-V center. A sufficient number of N-V centers must be created in order achieve a visible bulk luminescence emanating from within the synthetic diamond when excited using an ultraviolet lamp. An annealing time that is too short cannot produce enough N-V centers to show the required bulk luminescence. An annealing time that is too long will produce too many N-V centers which will change the starting color of the processed diamond.

Under the assumption that irradiation of the selected diamond is done following the previously discussed beam strengths, if the annealing time is too short, a visible bulk luminescence will not be created. On the other hand, if the annealing is too long, single Nitrogen atoms will pair with each other resulting in a so-called "A center" and Nitrogen atoms pairs will further pair with vacancies resulting in a so-called "H3 center."

Figure 8:
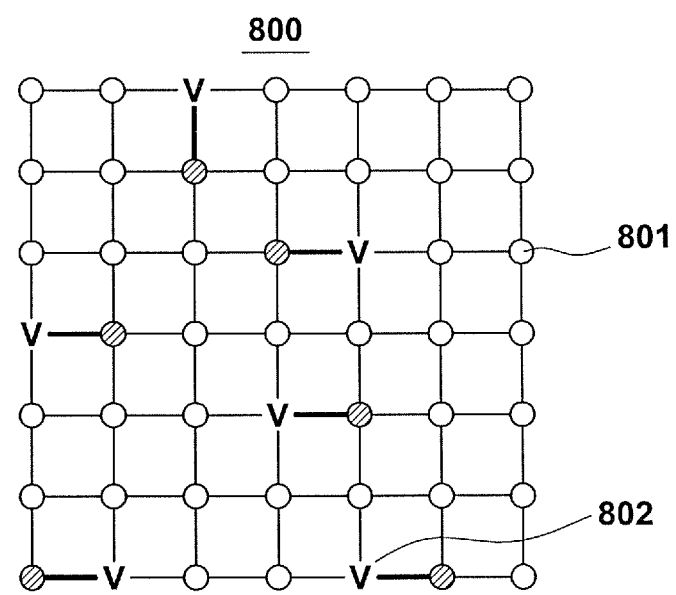
FIG. 8 is a two dimensional representation of the selected synthetic diamond lattice processed in the synthetic diamond labelling and identification method according to the disclosed embodiment.

In FIG. 8, a two dimensional representation of the selected synthetic diamond lattice processed in the synthetic diamond labelling and identification method according to the disclosed embodiment is shown. As shown in FIG. 8, the fully processed diamond lattice includes the original carbon atoms 801 as well as N-V centers 802 which have been formed as a result of annealing at a high temperature.

In FIG. 9, a table showing parameter used in the synthetic diamond labelling and identification method according to the disclosed embodiment is shown. As shown in FIG. 9, irradiation parameter 901 and annealing parameters 901 are defined. These irradiation and annealing parameters 901, 902 are organized according to the amount of single Nitrogen atoms in a selected diamond, specifically in first grouping 903 ranging from 200-600 ppb, a second grouping 904 ranging from 600-1000 ppb, and a third grouping 905 of 1 ppm or more. Within each of these single Nitrogen atom groupings, the irradiation parameters include carat size ranges of the selected diamond 906, irradiation beam strength 907, and irradiation duration 908.

Also within each of these single Nitrogen atom groupings, annealing durations are provided for two different types of annealing, namely high vacuum annealing at 900 degrees Celsius 909 and low pressure, high temperature ("LPHT") annealing at 1800 degrees Celsius 910.

Figure 10:
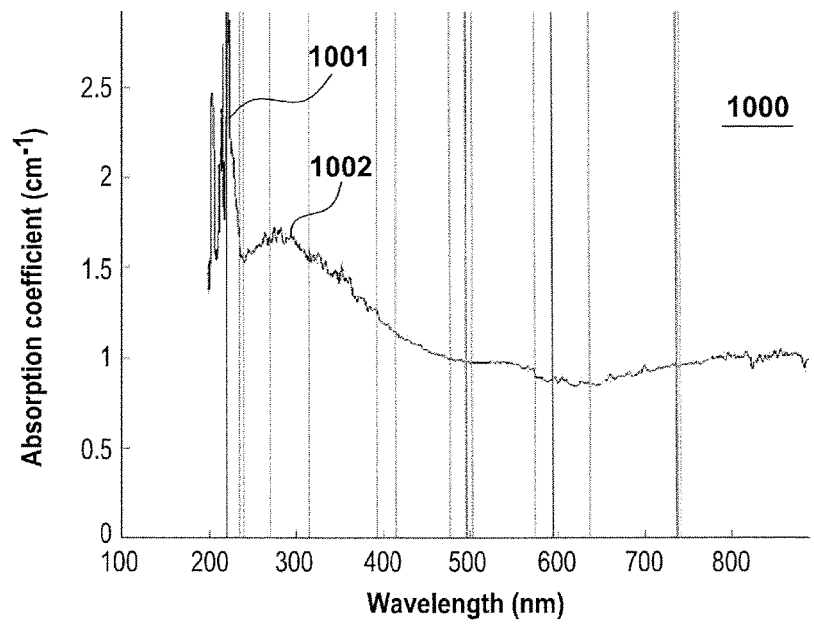
FIG. 10 is a spectroscopic absorption graph of the processed synthetic diamond in the synthetic diamond labelling and identification method according to the disclosed embodiment.

In FIG. 10, a spectroscopic absorption graph 1000 for a processed synthetic diamond in the synthetic diamond labelling and identification method according to the disclosed embodiment is shown. As shown in FIG. 10, similar to the absorption graph of a synthetic diamond prior to being processed, light is absorbed at the so-called absorption edge wavelength of 230 nanometers 1001 as well as at 270 nanometers 1002 which reflects the presence of isolated substitution (single) Nitrogen atom impurities. However, importantly, there is still some very low absorption in the visible range between 400 and 700 nanometers ensuring that the color of the processed synthetic diamond remains substantially the same and unaltered from its original color.

Figure 11:
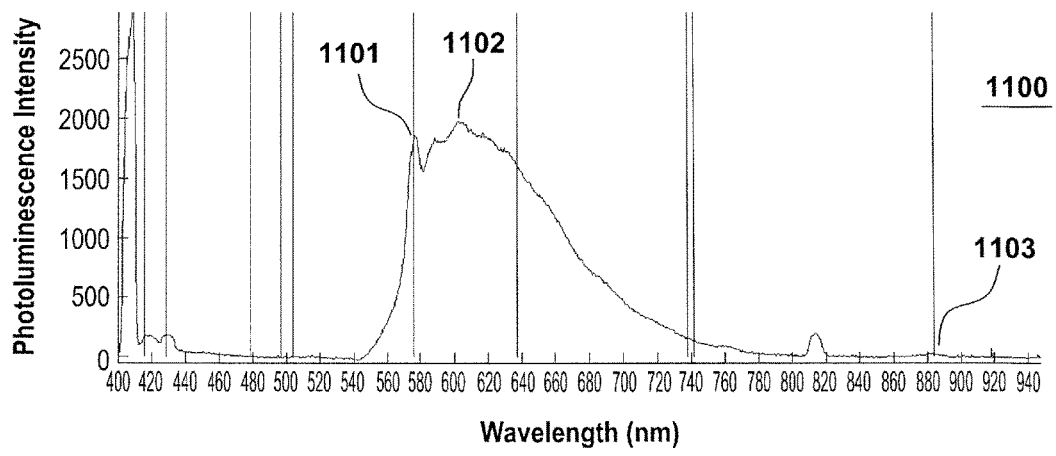
FIG. 11 a spectroscopic photoluminescence graph of the processed synthetic diamond in the synthetic diamond labelling and identification method according to the disclosed embodiment.

In FIG. 11, a spectroscopic photoluminescence graph 1100 for the processed synthetic diamond in the synthetic diamond labelling and identification method according to the disclosed embodiment is shown. As shown in FIG. 11, the processed synthetic diamond now exhibits a defined photoluminescence or fluorescence that can be induced by ultraviolet excitation which was not present prior to processing. The new photoluminescence is a result of the newly created N-V centers which emit light in the pink and red wavelengths range when excited using an ultraviolet lamp. Specifically, the photoluminescence has an emission band starting at 575 nanometers 1101 and spans with maximum of 610 nanometers 1102 that gradually decreasing up to 900 nanometers 1103.

What is claimed:

1. A synthetic diamond labelling and identification method comprising the steps:
    selecting a synthetic diamond with between 200 and 600 parts per billion of an isolated substitution Nitrogen atoms within its lattice structure;
    irradiating the selected synthetic diamond with a beam energy that is equal to at least one-half the height of the selected diamond;
    maintaining the temperature of the selected diamond below 500 degrees Celsius while it is being irradiated;
    annealing the irradiated selected diamond as to create a plurality of nitrogen-vacancy centers without changing the original color of the selected diamond; and
    generating a bulk luminesces visible to the naked eye by exciting the plurality of created nitrogen-vacancies with an ultraviolet lamp.

2. The synthetic diamond labelling and identification method of claim 1 wherein the annealing step is done in a vacuum at 900 degrees for a duration between 10 and 15 minutes.

3. The synthetic diamond labelling and identification method of claim 1 wherein the annealing step is done in hydrogen at 1800 degrees for a duration between 2 to 6 minutes.

4. The synthetic diamond labelling and identification method of claim 1 wherein the duration of the irradiation corresponds to the beam strength and the size of the selected diamond, the duration of irradiation being between 10 and 18 minutes.

5. A synthetic diamond labelling and identification method comprising the steps:
    selecting a synthetic diamond with between 600 and 1000 parts per billion of isolated substitution Nitrogen atoms within its lattice structure;
    irradiating the selected synthetic diamond with a beam energy that is equal to at least one-half the height of the selected diamond;

maintaining the temperature of the selected diamond below 500 degrees Celsius while it is being irradiated;

annealing the irradiated selected diamond as to create a plurality of nitrogen-vacancy centers without changing the original color of the selected diamond; and generating a bulk luminesces visible to the naked eye by exciting the plurality of created nitrogen-vacancies with an ultraviolet lamp.

6. The synthetic diamond labelling and identification method of claim 5 wherein the annealing step is done in a vacuum at 900 degrees for a duration between 9 and 13 minutes.

7. The synthetic diamond labelling and identification method of claim 5 wherein the annealing step is done in hydrogen at 1800 degrees for a duration between 2 to 4 minutes.

8. The synthetic diamond labelling and identification method of claim 5 wherein the duration of the irradiation corresponds to the beam strength and the size of the selected diamond, the duration of irradiation being between 8 and 15 minutes.

9. A synthetic diamond labelling and identification method comprising the steps:

selecting a synthetic diamond with more than 1000 parts per billion of isolated substitution Nitrogen atoms within its lattice structure;

irradiating the selected synthetic diamond with a beam energy that is equal to at least one-half the height of the selected diamond;

maintaining the temperature of the selected diamond below 500 degrees Celsius while it is being irradiated;

annealing the irradiated selected diamond as to create a plurality of nitrogen-vacancy centers without changing the original color of the selected diamond; and generating a bulk luminesces visible to the naked eye by exciting the plurality of created nitrogen-vacancies with an ultraviolet lamp.

10. The synthetic diamond labelling and identification method of claim 9 wherein the annealing step is done in a vacuum at 900 degrees for a duration of 8 to 12 minutes.

11. The synthetic diamond labelling and identification method of claim 9 wherein the annealing step is done in hydrogen at 1800 degrees for a duration of 1 to 3 minutes.

12. The synthetic diamond labelling and identification method of claim 9 wherein the duration of the irradiation corresponds to the beam strength and the size of the selected diamond, the duration of irradiation being 8 to 13 minutes.

* * * * *